United States Patent
Spahn

(10) Patent No.: US 7,428,294 B2
(45) Date of Patent: Sep. 23, 2008

(54) METHOD FOR RECORDING AN X-RAY IMAGE, AND X-RAY DETECTOR

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 29 days.

(21) Appl. No.: 11/527,613

(22) Filed: Sep. 27, 2006

(65) Prior Publication Data

US 2007/0071166 A1     Mar. 29, 2007

(30) Foreign Application Priority Data

Sep. 28, 2005    (DE) .................... 10 2005 046 414

(51) Int. Cl.
G01N 23/04    (2006.01)
(52) U.S. Cl. .................. 378/62; 378/98.8; 250/370.09
(58) Field of Classification Search ............. 378/4, 378/19, 62, 91, 98, 98.2, 98.7, 98.8, 116, 378/117; 250/366.1, 366, 370.08, 370.09
See application file for complete search history.

(56) References Cited

U.S. PATENT DOCUMENTS

| 5,583,905 | A | 12/1996 | Nishiki et al. ............. 378/98.8 |
| 5,818,898 | A | 10/1998 | Tsukamoto et al. ........ 378/98.8 |
| 5,923,722 | A | 7/1999 | Schulz .................... 378/98.8 |
| 2002/0150214 | A1 | 10/2002 | Spahn | |
| 2004/0228434 | A1* | 11/2004 | Tsujii ........................ 378/4 |

FOREIGN PATENT DOCUMENTS

| DE | 691 02 400T T2 | 2/1995 |
| DE | 196 31 624 C1 | 10/1997 |
| DE | 101 18 745 A1 | 10/2002 |
| DE | 101 18 745 C2 | 3/2003 |

OTHER PUBLICATIONS

M.Spahn et al.: "Digitale Röntgendetektoren in der Röntgendiagnostik", Der Radiologe 43, 2003, pp. 340-350.

* cited by examiner

Primary Examiner—Courtney Thomas
(74) Attorney, Agent, or Firm—Harness, Dickey & Pierce

(57) ABSTRACT

To speed up the availability of imaging data after the recording of an X-ray image, a method is disclosed. In the method, X-ray radiation emitted for an X-ray pulse duration is detected in an X-ray time window by an X-ray detector, and an X-ray image is recorded from it. Further, the width of the X-ray time window is continuously variably adjusted as a function of the X-ray pulse duration.

26 Claims, 2 Drawing Sheets

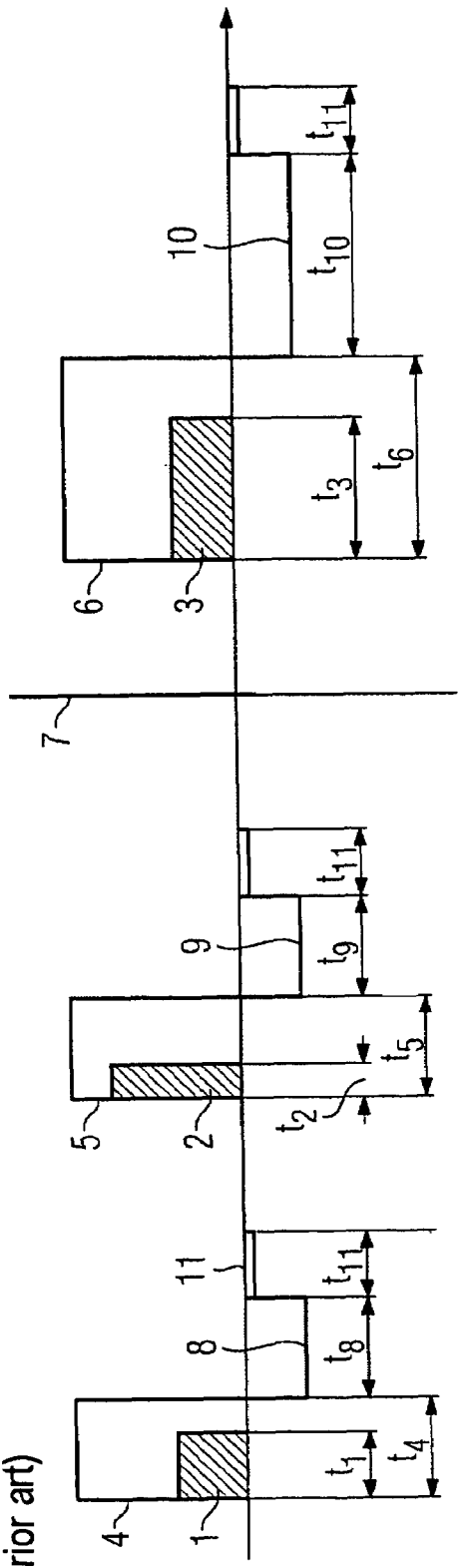
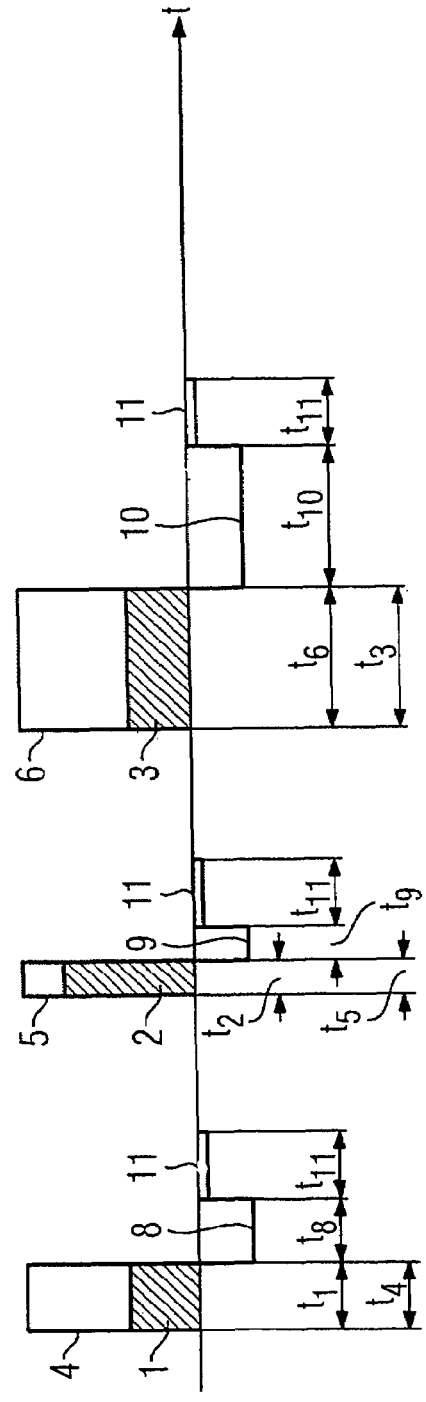
FIG 1 (Prior art)
FIG 2

METHOD FOR RECORDING AN X-RAY IMAGE, AND X-RAY DETECTOR

PRIORITY STATEMENT

The present application hereby claims priority under 35 U.S.C. §119 on German patent application number DE 10 2005 046 414.9 filed Sep. 28, 2005, the entire contents of which is hereby incorporated herein by reference.

1. Field

The invention generally relates to a method for recording an X-ray image, and to an X-ray detector.

2. Background

By way of example, image intensifier camera systems which are based on television or CCD cameras, storage film systems with an integrated or external read unit, systems with optical coupling of a converter film to CCD cameras or CMOS chips, selenic-based detectors with electrostatic reading and solid-state detectors with active read matrices and with direct or indirect conversion of the X-ray radiation are known in digital X-ray imaging.

In particular, solid-state detectors have been used for some years for digital X-ray imaging. These are based on active read matrices, for example composed of amorphous silicon, which are coated with a scintillator layer. The incident X-ray radiation is converted in the scintillator layer to visible light, is converted to electrical charge in light-sensitive pixel elements in the read matrix, and is stored on a position-resolved basis. Related technologies likewise use an active pixel matrix composed of amorphous silicon, but combined with an X-ray converter which converts the incident X-ray radiation directly to electrical charge. This is then stored on one electrode of the read matrix, on a position-resolved basis.

The time interval during which the active read matrix is switched to reception is referred to as the X-ray time window. In known solid-state detectors, the X-ray time window width is defined in advance. On the one hand, solid-state detectors are thus known in which only a single X-ray time window is provided, which must be sufficiently broad for all possible applications, and is thus as broad as the maximum X-ray pulse. On the other hand, solid-state detectors are known for which a small number of X-ray time windows are available, for example two or three predetermined X-ray time windows of different width. Adjustment of one of these X-ray time windows is thus possible only by switching the recording mode of the X-ray detector manually or in a controlled manner before the respective X-ray recording. Recording mode switching such as this generally at the same time results in the availability of correction maps, for example by uploading into a main memory.

In general, an offset image is recorded, and is subtracted from the X-ray image by way of electronic subtraction, in order to correct the noise and the offset in a raw X-ray image. In some applications, it is worthwhile recording the offset image directly after the recording of the raw X-ray image. This is the case in particular when the object being examined is repositioned immediately after the recording of a raw X-ray image, or when only a single X-ray image is produced.

SUMMARY

At least one embodiment of the present invention provides a method to allow imaging data recorded by an X-ray detector to be made available simply and as quickly as possible.

In the method according to at least one embodiment of the invention and in the X-ray detector according to at least one embodiment of the invention, because the width of the X-ray time window can be continuously variably adjusted as a function of the X-ray pulse duration, in particular such that it is equal to the X-ray pulse duration, the X-ray image data is made available as quickly as possible for each X-ray pulse duration in a simple manner, for example for passing on or for display on a monitor. The method according to at least one embodiment of the invention also avoids tedious and complex recording mode switching.

According to one refinement of an embodiment of the invention, the start of the X-ray time window is initiated by the start of the X-ray pulse, and the end of the X-ray time window is initiated by the end of the X-ray pulse. This can be achieved particularly easily by using a controller for an X-ray source which emits X-ray radiation to transmit control signals relating to the start and the end of the X-ray pulse to the X-ray detector. This makes it possible, overall, to ensure that, on the one hand, the entire X-ray pulse is used for imaging and that, on the other hand, the X-ray rime window is no broader than is necessary on the basis of the X-ray pulse.

An offset image for correction of the X-ray image is advantageously recorded immediately after the recording of the X-ray image. This makes it possible to make an offset-corrected X-ray image available quickly as well, provided that the correction process is likewise carried out close to real time. In addition, and in contrast to an offset image recorded before the X-ray image, it is thus possible to reduce lag effects and ghosting artifacts. In addition, the amount of data to be transferred from the X-ray detector to an image system can be reduced because the offset image can be subtracted from the X-ray image directly in the X-ray detector. This may be advantageous, in particular for slow data transmission rates, for example in the case of wire-free data transmission.

The recording of an offset image for correction of the X-ray image immediately after the recording of the X-ray image is also advantageous because the working process cannot be disadvantageously influenced in this way, if the offset image has already been recorded before the next recording is requested (for example after repositioning of the patient).

According to one further refinement of an embodiment of the invention, the recording duration of the offset image corresponds to the width of the X-ray time window. The respective X-ray pulse duration is expediently—at least briefly—measured and stored for an effective and simple implementation of this.

According to one refinement of an embodiment of the invention, an X-ray detector which is suitable for the method has an associated radiation source for transmission of the X-ray radiation. According to further refinements of embodiments of the invention, the X-ray detector also has an associated image processing unit for storage of an offset image and for correction of the X-ray image with the aid of the offset image, and an associated control device for driving the width of the X-ray time window.

The control device for driving the width of the X-ray time window and for driving the pulse duration of the X-ray pulse is advantageously used for simple matching of the X-ray time window width to the X-ray pulse duration.

BRIEF DESCRIPTION OF THE DRAWINGS

The invention as well as further advantageous refinements based on features of the dependent claims will be explained in more detail in the following text using a schematically illustrated example embodiment in the drawings, without the invention being restricted to this example embodiment. In the drawings:

FIG. 1 shows a timing diagram of three X-ray recordings with associated offset recordings according to the prior art;

FIG. 2 shows a timing diagram of three successively recorded X-ray recordings and associated offset recordings using a method according to an embodiment of the invention;

DETAILED DESCRIPTION OF THE EXAMPLE EMBODIMENTS

Figure 3:
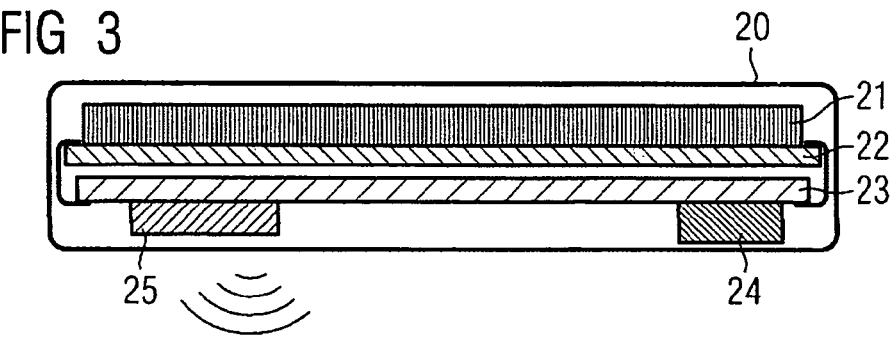
FIG. 3 shows an X-ray detector according to an embodiment of the invention.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a sequence of three X-ray time windows 4-6 along a time axis t, which form a known method according to the prior art. At the start of the respective X-ray time window 4-6, an X-ray detector is in a previously defined recording mode, which fixes the width $t_4$-$t_6$ of the respective X-ray time window 4-6, further recording parameters as well as various correction maps. In this recording mode, the respective, fixed associated X-ray time window 4-6 has a defined time width which is of adequate size in order to ensure that every X-ray pulse 1-3 which is possible in this recording mode fits into the X-ray time window 4-6. The X-ray pulse duration $t_1$ of a first X-ray pulse 1 is thus at most as long as the X-ray time window width $t_4$ of a first X-ray time window 4.

In general, the X-ray pulse duration $t_1$-$t_3$ of the X-ray pulses 1-3 is, however, considerably shorter than the X-ray time window width $t_4$-$t_6$ of the respective X-ray time window 4-6. In FIG. 1, the X-ray pulse duration $t_1$ of the first X-ray pulse 1 is shorter than the X-ray time window width $t_4$ of the first X-ray time window 4. In the same way, the X-ray pulse duration $t_2$ of the second X-ray pulse 2 is shorter than the X-ray time window width $t_5$ of the second X-ray time window 5. In general, in the prior art, the recording duration $t_8$-$t_{10}$ of the offset recordings 8-10 is fixed to correspond to the X-ray time window width $t_4$-$t_6$ of the X-ray time windows 4-6. The recording duration $t_8$ of the first offset recording 8 is thus likewise of the same magnitude as the X-ray time window width $t_4$ of the first X-ray time window 4.

In a corresponding manner, the recording duration $t_9$ of the second offset recording 9 is also precisely of the same magnitude as the X-ray time window width $t_5$ of the second X-ray time window 5. Since the X-ray detector for the first X-ray recording and for the second X-ray recording are in the same recording mode, the first X-ray time window 4 corresponds to the second X-ray time window 5. The corresponding offset recordings 8; 9 are recorded after the X-ray recordings, in order to reduce lag effects and in order to make it possible to correct the X-ray image directly by means of the offset image in the X-ray detector. The object being examined can, for example, be repositioned between a first X-ray recording and a second X-ray recording. After the offset recordings 8; 9; 10, an offset correction process 11 is in each case carried out for a correction duration $t_{11}$.

Recording mode switching 7 takes place after the second X-ray recording. This recording mode switching 7 fixes the X-ray time window length $t_6$ of the subsequent X-ray time window, that is to say by way of example the third X-ray time window 6. The third X-ray pulse 3 is arranged within the third X-ray time window 6, and the X-ray time window width $t_6$ of the third X-ray time window 6 is in general likewise longer than the X-ray pulse duration $t_3$ of the third X-ray pulse 3. A recording duration $t_{10}$ for a third offset recording 10 is once again fixed by the X-ray time window width $t_6$ of the third X-ray time window 6. The X-ray time window widths of the X-ray time windows are not flexible.

In contrast to the prior art, the width of the X-ray time window in the case of at least one embodiment of the invention can be continuously variably adjusted as a function of the X-ray pulse duration.

FIG. 2 shows a timing diagram of three successive X-ray recordings using the method according to an embodiment of the invention and using an X-ray detector according to the invention. The X-ray pulse duration $t_1$ of the first X-ray pulse 1 is in this case precisely the same length as the X-ray time window width $t_4$ of the first X-ray time window 4. The first, second and third X-ray time windows 4, 5 and 6 are variable, and can be adjusted independently of the recording mode. The associated X-ray time window widths $t_4$, $t_5$ and $t_6$ are defined by the X-ray pulse durations $t_1$, $t_2$ and $t_3$ of the first, second and third X-ray pulses 1, 2 and 3.

It is advantageous for the start and the end of the respective X-ray time window 4-6 to coincide with the start and the end of the respective X-ray pulse 1-3. In this context, one refinement of an embodiment of the invention provides for a control device for an X-ray source, which emits X-ray radiation, to transmit control signals or information relating to the start and the end of the X-ray pulse to the X-ray detector. For example, this may be done automatically.

The X-ray detector uses the control signals to drive the X-ray time window 4-6, such that the width $t_4$-$t_6$ of the X-ray time window 4-6 is equal to the pulse duration $t_1$-$t_3$ of the X-ray pulse 1-3. A system control device 28 for an X-ray recording system 31 can also be provided for transmission of the control signals, associated with the X-ray source 27 and the X-ray detector and connected to them for communication purposes. The system control device 28 for the X-ray image recording system 31 may also at the same time send control signals such as "X-ray on" or "X-ray off" to the X-ray source 27 and to the X-ray detector, thus ensuring that the X-ray time window 4-6 and the X-ray pulse 1-3 start and end simultaneously. The control signals are preferably transmitted without the use of cables, for example by way of radio links, between the X-ray image recording system 31 and the X-ray detector, as well as between the X-ray image recording system 31 and the X-ray source 27.

An offset image is advantageously recorded immediately after the recording of the X-ray image, in order to correct the X-ray image. For rapid availability of the imaging data, the recording duration $t_8$-$t_{10}$ of the offset image, in particular, advantageously corresponds to the width $t_4$-$t_6$ of the X-ray time window 4-6. In order to ensure this, according to one refinement of an embodiment of the invention, the X-ray detector measures the pulse duration $t_1$-$t_3$ of the X-ray pulse 1-3 or the width $t_4$-$t_6$ of the X-ray time window 4-6 and stores this at least until the recording duration $t_8$-$t_{10}$ of the offset image has been fixed or the recording of the offset image has been initiated. The information relating to the pulse duration $t_1$-$t_3$ of the X-ray pulse 1-3 or the width $t_4$-$t_6$ of the X-ray time window 4-6 is used by the X-ray detector to define the recording duration $t_8$-$t_{10}$ of the offset images.

Overall, at least one embodiment of the invention restricts, and thus minimizes, the X-ray time window width $t_4$-$t_6$ to precisely the width $t_4$-$t_6$ that is defined by the X-ray pulse 1-3 and is required for the corresponding application. This also applies to the respective offset image, whose recording duration $t_8$-$t_{10}$ corresponds, according to one refinement of an embodiment of the invention, to the width $t_4$-$t_6$ of the X-ray time window 4-6, and is thus likewise a minimum. Once the respective offset recording 8-10 has been recorded, the offset image is corrected in the X-ray image recording system 31, for example directly in the X-ray detector, by way of an offset correction process 11 for a correction duration $t_{11}$. The offset correction process 11 generally comprises subtraction of the offset image from the X-ray image. The method according to an embodiment of the invention thus results in the image data being available after a time which is as short as possible for further image processing or, for example, for display on a monitor, in general considerably more quickly than in the prior art.

The information (that is stored in the X-ray detector) relating to the X-ray time window width $t_4$-$t_6$ can be used not only for the recording of the offset image but also for gain corrections and defect corrections. Since, in general, gain images and defect images are determined in a calibration process before the recording of the X-ray image, the recording durations of gain images and defect images do not precisely match the width $t_4$-$t_6$ of the X-ray time window 4-6 of the respective X-ray image. The information relating to the X-ray time window width $t_4$-$t_6$ or the pulse duration $t_1$-$t_3$ of the X-ray pulse 1-3 can be used to select the gain image or the defect image whose recording duration best matches the X-ray time window width $t_4$-$t_6$ or the pulse duration $t_1$-$t_3$ of the X-ray pulse 1-3 of the respective X-ray image. This in turn can be done automatically by way of a control device or by means of an image processing unit.

According to one further refinement of an embodiment of the invention, the X-ray detector is in the form of a flat image detector 20, in particular a mobile flat image detector without any cables. FIG. 3 shows one such flat image detector 20 having a scintillator layer 21, an active matrix 22, an electronics board 23, a power supply unit 24 and a data transmission and communication unit 25 for transmission of imaging data and control commands without the use of cables.

Figure 4:
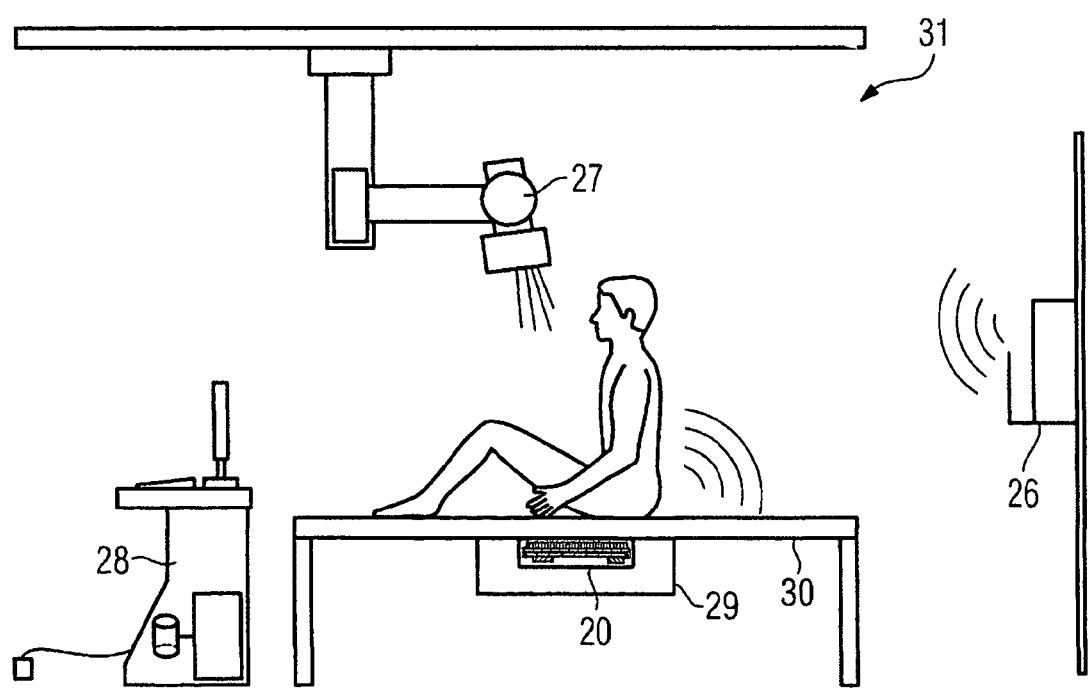
FIG. 4 shows an X-ray image recording system having an X-ray detector as shown in FIG. 3.

In order to carry out a method according to an embodiment of the invention, the flat image detector 20 has an associated X-ray image recording system 31—as is shown in FIG. 4—and is connected for communication and data transmission processes to a loading station 26. The X-ray image recording system 31 has, in addition to the loading station, a system control device 28 and an X-ray source 27 for transmission of X-ray radiation. The system control device 28 has an image processing unit, a control device for driving the X-ray source 27 and the flat image detector 20, and a display apparatus, for example a monitor.

The X-ray source 27 is mounted, for example by way of an arm which can pivot, on the ceiling of a room, and the flat image detector is located in a Bucky drawer 29 of a Bucky table 30. In addition, the flat image detector 20 may likewise have an image processing unit (not shown) which can be used to carry out an offset correction. A flat image detector 20 such as this results in offset-corrected X-ray images being available particularly quickly. In addition, the amount of data to be transmitted is reduced by offset correction being carried out in the flat image detector 20 itself.

In addition to the described method, in which the duration $t_1$-$t_3$ of the X-ray pulse 1-3 corresponds to the width $t_4$-$t_6$ of the X-ray time window 4-6, and the start and the end of the X-ray pulse 1-3 and X-ray time window 4-6 coincide, it is also possible to provide for the X-ray time window width $t_4$-$t_6$ to be driven in such a manner that it is slightly longer than the X-ray pulse duration $t_1$-$t_3$.

At least one embodiment of the invention can be summarized briefly as follows: In order to speed up the availability of imaging data after the recording of an X-ray image, a method is provided in which X-ray radiation which is emitted for an X-ray pulse duration is detected in an X-ray time window by an X-ray detector, and an X-ray image is recorded from it, and in which the width of the X-ray time window is continuously variably adjusted as a function of the X-ray pulse duration.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for recording an X-ray image, comprising:
   detecting X-ray radiation, emitted for an X-ray pulse duration, in an X-ray time window by an X-ray detector, a width of the X-ray time window being continuously variably adjusted as a function of the X-ray pulse duration; and
   recording an X-ray image from the detected X-ray radiation.

2. The method as claimed in claim 1, wherein the width of the X-ray time window is equal to the X-ray pulse duration.

3. The method as claimed in claim 1, wherein a start and an end of the X-ray time window coincide with a start and an end of the X-ray pulse.

4. The method as claimed in claim 3, wherein the start of the X-ray time window is initiated by the start of the X-ray pulse, and the end of the X-ray time window is initiated by the end of the X-ray pulse.

5. The method as claimed in claim 4, wherein a control device for an X-ray source to emit X-ray radiation, transmits control signals relating to the start and the end of the X-ray pulse to the X-ray detector.

6. The method as claimed in claim 4, wherein a control device, in an X-ray recording system including the X-ray source that emits X-ray radiation and the X-ray detector, controls the start and the end of the X-ray pulse and of the X-ray time window.

7. The method as claimed in claim 1, wherein an offset image is recorded immediately after the recording of the X-ray image, in order to correct the X-ray image.

8. The method as claimed in claim 1, wherein the recording duration of the offset image corresponds to the width of the X-ray time window.

9. The method as claimed in claim 1, wherein the X-ray image is corrected by use of the offset image.

10. The method as claimed in claim 1, wherein the respective X-ray pulse duration is measured and stored.

11. A computer readable medium including program segments for, when executed on a computer device, causing the computer device to implement the method of claim 1.

12. An X-ray detector comprising:
    a detection device configured to detect X-ray radiation for an X-ray pulse duration in an X-ray time window; and
    an electronics board configured to record an X-ray image based on the detected X-ray radiation,
    wherein a width of the X-ray time window being continuously variably adjustable as a function of the X-ray pulse duration.

13. The X-ray detector as claimed in claim 12, wherein the detection device includes
    a scintillator layer receiving the X-ray radiation and converting the X-ray radiation to information detectable by an active matrix; and
    the active matrix detecting the information for the X-ray pulse duration in the X-ray time window.

14. The X-ray detector as claimed in claim 12, wherein the electronics board of the X-ray detector includes an associated image processing unit configured to store an offset image and configured to correct the X-ray image with the aid of the offset image.

15. The X-ray detector as claimed in claim 12, wherein the recording duration of the offset image, for correction of the respective X-ray image, corresponds to the width of the X-ray time window of the X-ray image.

16. The X-ray detector as claimed in claim 12, wherein the electronics board of the X-ray detector includes an associated control device configured to drive the width of the X-ray time window.

17. The X-ray detector as claimed in claim 12, wherein the electronics board of the X-ray detector includes an associated control device configured to drive the width of the X-ray time window, and the pulse duration of the X-ray pulse.

18. The X-ray detector as claimed in claim 12, wherein the X-ray detector is in the form of a flat image detector.

19. The X-ray detector as claimed in claim 18, wherein the flat image detector is designed to be mobile, without any cables.

20. An X-ray image recording system, comprising:
    the X-ray detector as claimed in claim 12;
    an X-ray source configured to transmit the X-ray radiation for the X-ray pulse duration; and
    a control device configured to drive the width of the X-ray time window and the pulse duration of the X-ray pulse.

21. A detector for recording an X-ray image, comprising:
    means for detecting X-ray radiation, emitted for an X-ray pulse duration, in an X-ray time window by an X-ray detector, a width of the X-ray time window being continuously variably adjusted as a function of the X-ray pulse duration; and
    means for recording an X-ray image from the detected X-ray radiation.

22. An X-ray image recording system, comprising:
    the X-ray detector as claimed in claim 21;
    an X-ray source configured to transmit X-ray radiation for an X-ray pulse duration; and
    a control device configured to drive the width of the X-ray time window and for driving the pulse duration of the X-ray pulse.

23. An X-ray detector, comprising:
    means for detecting X-ray radiation, emitted by an X-ray source, for an X-ray pulse duration in an X-ray time window, and
    means for recording an X-ray image from the detected X-ray radiation, a width of the X-ray time window being continuously variably adjustable as a function of the X-ray pulse duration.

24. The X-ray detector as claimed in claim 23, further comprising:
    means for transmission of the X-ray radiation.

25. The X-ray detector as claimed in claim 23, further comprising:
    means for storage of an offset image and for correction of the X-ray image with the aid of the offset image.

26. An X-ray image recording system, comprising:
    the X-ray detector as claimed in claim 23;
    an X-ray source configured to transmit the X-ray radiation for an X-ray pulse duration; and
    a control device configured to drive the width of the X-ray time window and the pulse duration of the X-ray pulse.

* * * * *